United States Patent [19]
Robinson

[11] Patent Number: 5,839,899
[45] Date of Patent: Nov. 24, 1998

[54] METHOD AND APPARATUS FOR GROWING JAW BONE UTILIZING A GUIDED-TISSUE REGENERATION PLATE SUPPORT AND FIXATION SYSTEM

[76] Inventor: Dane Q. Robinson, 8330 E. Captain Dreyfus, Scottsdale, Ariz. 85260

[21] Appl. No.: 609,870

[22] Filed: Mar. 1, 1996

[51] Int. Cl.⁶ .............................. A61C 8/00; A61F 2/28; A61L 31/00
[52] U.S. Cl. ............................. 433/215; 433/173; 623/16
[58] Field of Search ..................... 433/167, 173, 433/174, 215; 606/53, 69, 70; 623/16

[56] References Cited

U.S. PATENT DOCUMENTS

| | | | |
|---|---|---|---|
| 3,849,805 | 11/1974 | Leake et al. | 623/16 |
| 4,531,916 | 7/1985 | Scantlebury et al. | 433/173 |
| 4,636,215 | 1/1987 | Schwartz | 623/16 |
| 4,787,906 | 11/1988 | Harris | 623/16 |
| 4,863,383 | 9/1989 | Grafelman | 433/174 |
| 4,961,707 | 10/1990 | Magnusson et al. | |
| 5,071,351 | 12/1991 | Green, Jr. et al. | 433/174 |
| 5,145,371 | 9/1992 | Jörnéus | 433/174 |
| 5,297,563 | 3/1994 | Syers . | |
| 5,372,503 | 12/1994 | Elia | 433/215 |
| 5,378,152 | 1/1995 | Elia | 433/215 |
| 5,380,328 | 1/1995 | Morgan . | |
| 5,397,235 | 3/1995 | Elia | 433/173 |

FOREIGN PATENT DOCUMENTS

| | | | |
|---|---|---|---|
| 622052 | 11/1994 | European Pat. Off. | 623/16 |
| 2647665 | 12/1990 | France | 606/69 |
| 4232511 | 3/1994 | Germany | 433/174 |
| 679117 | 12/1991 | Switzerland | 433/173 |
| 8803391 | 5/1988 | WIPO | 433/174 |
| 9403121 | 2/1994 | WIPO | 433/215 |

*Primary Examiner*—Ralph A. Lewis
*Attorney, Agent, or Firm*—James H. Phillips; Squire, Sanders & Dempsey

[57] ABSTRACT

A method of growing jaw bone and the related guided-tissue regeneration plate support and fixation system employed in the method where an isolated and protected space free from tissue impingement, occlusal loading, chewing forces or muscular pressure is created between the periosteum and the jaw bone. This space is created by first placing either a dental implant or a guided-tissue regeneration plate support and fixation system tenting-type support screw into the jaw bone. The plate portion of the guided-tissue regeneration plate support and fixation system, preferably made out of Grade 1 commercially pure titanium, being thicker and more rigid in the center, more supportive area and thinner at the periphery is either snapped-down onto the head of the support screw or onto a specialized and modified healing screw of a dental implant which has a receiver cap or is screwed directly into a dental implant. The plate is then bent and molded into the proper shape. In essence, the pliable, moldable plate is both supported by the dental implant or support screw and fixed into place by the same screw creating both support and fixation of the plate giving a precise space below its surface to grow bone. This plate portion can be solid or perforated, and it can be porous or non-porous.

24 Claims, 3 Drawing Sheets

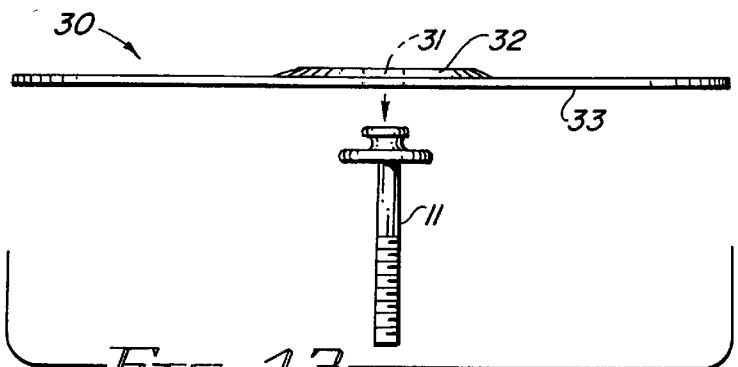
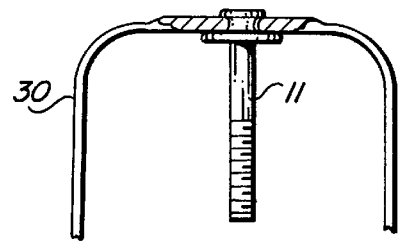
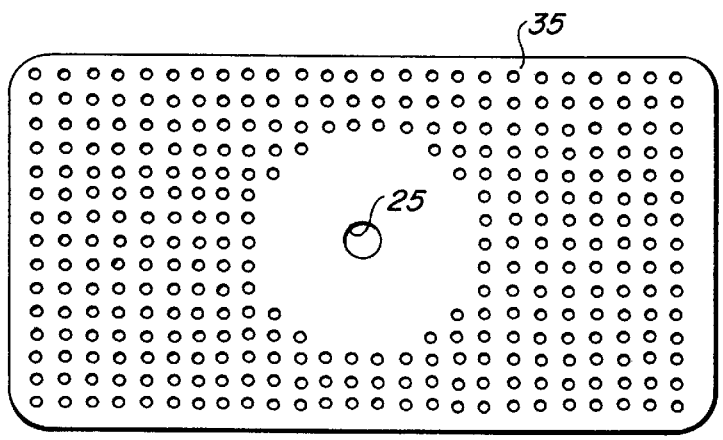
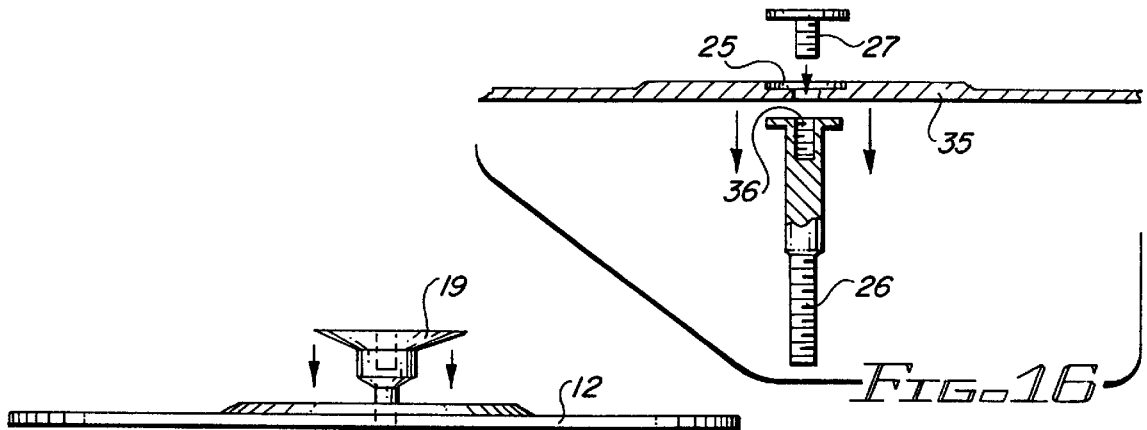
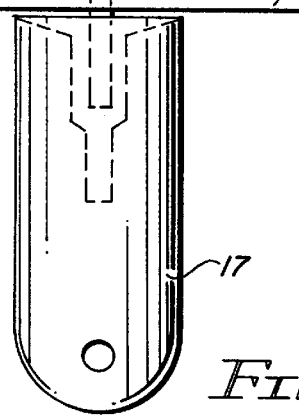

METHOD AND APPARATUS FOR GROWING JAW BONE UTILIZING A GUIDED-TISSUE REGENERATION PLATE SUPPORT AND FIXATION SYSTEM

FIELD OF THE INVENTION

This invention relates to the art of dentistry and, more particularly, to a method and devices thereof which relate to the surgical placement of endosseous dental implants in the maxillary or mandibular jaw bone. Still more specifically, this invention relates to the growing of jaw bone in order to obtain adequate volume of osseous structure by using a thin titanium bone plate which is mated to an underlying support bone screw or to a dental implant.

BACKGROUND OF THE INVENTION

The successful placement of endosseous dental implants has been well documented for over 30 years; however, the success of these endosseous dental implants has been limited by the quality and quantity of existing bone a given patient would present with. Due to the destructive nature of dentures to the underlying jaw bone as well as the fact that bone that is not internally stimulated by tooth roots will atrophy, the amount of bone in many people is very limited for the placement of dental implants, especially for those who have been missing teeth for an extended period of time.

Bone grafting has become an essential element for the successful treatment of those who do not have enough bone for dental implants. As viable methods, blocks of hip bone have been affixed to the jaw and freeze-dried demineralized bone protein has been used as a stimulant to cause the patient's bone cells to become active and lay down new bone onto the existing bone areas and into the new bone graft areas. Through experience and research, it has become evident that, for bone grafting to be successful, it must be given an isolated space to grow, protected from muscular pressure, tissue impingement and chewing forces. In order to create this space, many approaches have been proposed. For example, both Syers (U.S. Pat. No. 5,297,563) and Magnusson et al (U.S. Pat. No. 4,961,707) teach the use of a fabric-like membrane which is used over a bony defect. Although this barrier creates an isolated space from the invasion of epithelial cells into the bony defect or bone graft area, it does not create a protected space from chewing forces or tissue pressure.

Morgan (U.S. Pat. No. 5,380,328) teaches the use of a composite perforated titanium mesh layered with polytetrafluoraethylene (PTFE or Teflon®) fibers. Even though this approach would be feasible for creating a protected space in order to grow bone, it has some severe limitations. This material requires the placement of peripheral bone screws into the edges of the meshed piece in order to create a direct fixation of the titanium mesh to the jaw bone and then bowing-up or tenting-up the center area in order to create the protected space. Often, it would not be feasible to place the peripheral bone screws in the peripheral areas for fear of damage to the inferior alveolar nerves or sinus penetration or damage to nearby tooth roots. The protrusion of these screws above the mesh is also of concern as potentially causing a tissue irritation complication with this given procedure. Furthermore, the difficulty of forming the exact amount of tenting desired with this material is inherently very difficult to control. Additionally, the removal of this material is complicated by the need to surgically dissect much deeper to locate the peripheral screws. This technique would also be expensive and time consuming to emplace due to the need for multiple screws to secure a single mesh.

On the other hand, as will become more apparent below, the guided-tissue regeneration plate support and fixation system contemplated in accordance with the subject invention obtains the ability to place a single screw in the center of the bone graft area, thereby facilitating the selection of a screw height that allows for an exact amount of tenting, thus giving the support where it is needed most. Placement and removal of this device is greatly simplified due to the fact that peripheral screws are not required. The head of the screw ends up being mostly under the plate, thus preventing any concern about screw-head irritation or protrusion. Furthermore, concern about damage to neighboring peripheral structures is eliminated. In general, a much more simplified and cost effective method, apparatus and result are achieved.

OBJECTS OF THE INVENTION

It is therefore a broad object of my invention to provide an improved dental implant system.

It is a more specific object of my invention o provide an improved dental implant system which is relatively inexpensive to fabricate and use.

In another aspect, it is an object of my invention to provide a dental implant system which is relatively easy to use and to obtain high quality results.

SUMMARY OF THE INVENTION

Briefly, these and other objects of the invention are achieved by a method of growing additional maxillary or mandibular bone in areas of atrophy and by the use of a related device to accomplish the task. A pliable guided-tissue regeneration plate, which holds it shape after being bent, is employed as a mating component to a support screw or a dental implant and is secured to the jaw structure by fixation of the guided-tissue regeneration plate at a predetermined distance above or away from the surface of the bone to the support screw or dental implant in order to create a supported and protected space between the underside of the gum tissue and the bone which is free from muscular and chewing pressure in order to promote bone growth. The guided-tissue regeneration plate support and fixation system can be mated with a support screw or screws which are tenting screws designed to be mated with and then become intimately a part of the guided-tissue regeneration plate in order to grow bone in the space created by the guided-tissue regeneration plate system prior to implant placement. Additionally, the guided-tissue regeneration plate system can be utilized during implant placement by creating space adjacent to a dehisced implant by fixation of the guided-tissue regeneration plate directly to the implant in order to grow bone height or width. A guided-tissue regeneration plate according to the present invention can also be used by affixing it to an existing dental implant that has been previously placed and has undergone bone loss in order to regenerate new bone. The guided-tissue regeneration plate support and fixation system is adapted to be surgically removed after the bone has grown under its surface at a later uncovering or implant placement surgery.

DESCRIPTION OF THE DRAWING

The subject matter of the invention is particularly pointed out and distinctly claimed in the concluding portion of the specification. The invention, however, both as to organization and method of operation, may best be understood by reference to the following description taken in conjunction with the subjoined claims and the accompanying drawing of which:

FIG. 13 illustrates a snap configured support screw ready to receive a guided-tissue regeneration plate;

FIG. 14 depicts the guided-tissue regeneration plate over the snap configured support screw after the edges have been bent down to create a space below the guided-tissue regeneration plate;

FIG. 15 illustrates a perforated version of the guided-tissue regeneration plate;

FIG. 16 depicts a guided-tissue regeneration plate being secured to a guided-tissue regeneration plate support screw by a small set screw; and FIG. 17 illustrates the manner in which an exemplary healing screw of the sort typically supplied by a dental implant manufacturer can be employed to secure the guided-tissue regeneration plate to a dental implant.

DETAILED DESCRIPTION OF THE PREFERRED EMBODIMENTS

Figure 1:
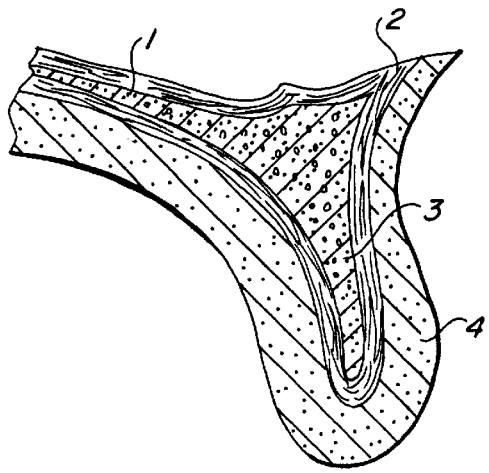
FIG. 1 illustrates a bony ridge that has undergone substantial loss.

The described invention relates to a method of growing jaw bone and to the related guided-tissue regeneration plate support and fixation system by which an isolated and protected space free from tissue impingement, occlusal loading, chewing forces, or muscular pressure is created between the periosteum and the jaw bone. This space is created by first placing either a dental implant or a guided-tissue regeneration plate support and fixation system tenting-type support screw into the jaw bone and then coupling the guided-tissue regeneration plate to the support screw.

The presently preferred embodiment of the support screws, preferably made out of (but not limited to) titanium, are thin shafted screws with a relatively high ratio between the greater diameter to the minor diameter of the threads to give the maximum bite and hold into the bone. Preferably, this ratio is at least two. The head of the tenting-type support screw is placed above or away from the bone a suitable distance of the space created in order to grow bone. The screw head is configured to receive the guided-tissue regeneration plate, thus allowing for most of the head to be either in or under the guided-tissue regeneration plate after it is engaged into a receiver cap of the head.

In another contemplated embodiment of the support screws, the head of the support screw is internally axially threaded or is provided with a threaded or non-threaded well allowing for a pin with a small head resembling a micro thumbtack to extend through the guided-tissue regeneration plate into the well and snap or thread into place, thereby securing the guided-tissue regeneration plate to the head of the tenting-type support screw. The support screw is preferably fabricated to be very sharp at its tip which includes a self-starting flute in order to facilitate self-threading for facilitating placement.

The guided-tissue regeneration plate is preferably made of thin titanium sheet metal having a peripheral thickness of around 5 to 10 thousandths of an inch. This thickness allows for the material to be thin enough to be bent into shape, but rigid enough to hold its shape after being bent and molded. The present material of choice is Grade 1 titanium which is the fully annealed form of titanium advantageously characterized in that it will not spring back after being bent.

The plates are fabricated with a precise aperture proximate the center or wherever needed in order to allow for a precise union and mating to the support screw or receiver cap of the healing screw of a dental implant, thus giving a secure fixation, by indirect means, to the jaw bone. The central area of the guided-tissue regeneration plate is preferably thicker in order to provide more support and rigidity than the peripheral region. The combination of the support screw and the thicker area of the plate near the center prevents the guided-tissue regeneration plate from caving-in in the area where maximum support is needed when overlying pressure, such as muscular pressure, chewing forces, or any other premature loading onto the guided-tissue regeneration plate support and fixation system, is later applied.

The guided-tissue regeneration plate can optionally be perforated to allow for better overlying tissue healing as well as to promote the exchange of nutrients and blood supply between the bone graft and the overlying tissue. Generally, the central, thicker, more supportive area is not perforated to obtain more support. Typically, the number and size of the perforations is less concentrated than the amount of solid space to create a more supportive plate at a thinner dimension. If a completely imperforate barrier is desired to isolate all transfer of unwanted epithelial cells into the bone graft area, then the guided-tissue regeneration plate is fabricated imperforate except for the generally centrally disposed aperture for fixing the plate to its support screw.

However, if a temporary period of isolation from epithelial cells is desired to create a membrane barrier from epithelial cells for a limited period of time which allows for the exchange of nutrients, ions, and tissue fluid or perhaps blood supply, then a resorbable barrier such as vicryl, collagen, resorbable hydroxyapatite crystals or Guidor™ can be applied to the under or over side of the guided-tissue regeneration plate to seal the perforations, then resorbing a limited time later after the system is installed.

If a non-resorbable semi-permeable result is desired, then the perforations can be covered by applying a suitable material such as PTFE fibers. After a period of several months have passed, the entire system is removed and then the implants are either simultaneously placed during this surgery or uncovered by placing healing caps into the implants. If the only desired effect is to create a better ridge for the stabilization of a denture, then the system may be left in place indefinitely.

Having now discussed the fundamentals of the present invention, attention is invited to the several FIGs. for an alternative and clarifying disclosure as the discussion proceeds.

FIG. 1 shows an exemplary existing midline cross-section of a maxillary edentulous ridge which has undergone substantial bone loss. For orientation purposes, landmarks can be identified by the palatal bone 1, the floor of the nose 2, the bony ridge 3, and the gum tissue 4.

Figure 2:
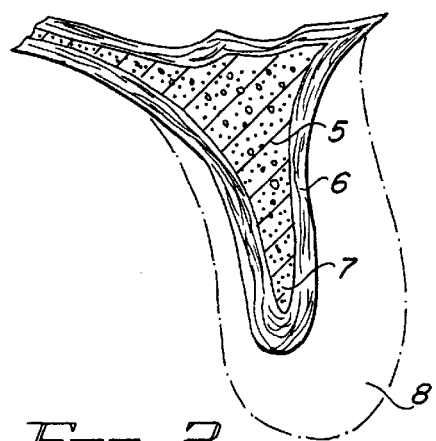
FIG. 2 depicts a cross-section of a maxillary midline area of an edentulous ridge showing the original size prior to bone loss.

FIG. 2 depicts a cross-section of a maxillary midline area of an edentulous ridge showing the original size prior to bone loss (the gum tissue is not shown in this view).. Reference is taken to the narrow space 5, the cortical bone 6 and the current size of the ridge 7 after bone loss and to the area of the original size 8 of the ridge prior to atrophy or bone loss.

Figure 3:
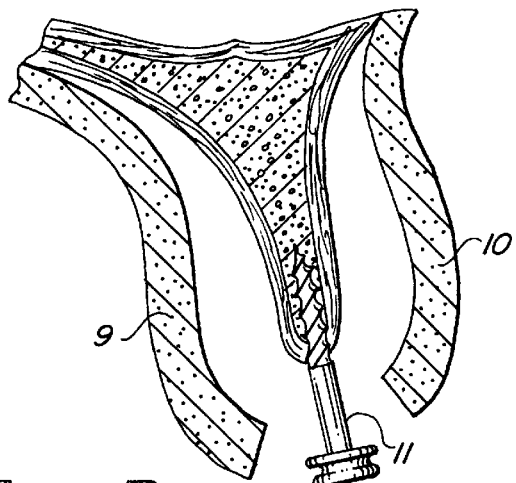
FIG. 3 shows the surrounding tissue first reflected away from the bony ridge to expose the ridge in its entirety.

Referring now to FIG. 3, in order to place a guided-tissue regeneration plate support and fixation system according to the present invention, the tissue is first reflected away from the bony ridge to expose the ridge in its entirety. The palatal gum tissue 9 is reflected 9, the facial gum tissue 10 is reflected, and a guided-tissue regeneration plate support screw 11 is placed into the bony ridge.

Figure 4:
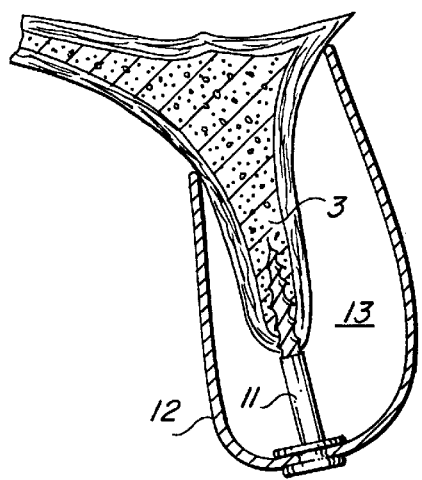
FIG. 4 depicts the mating of a guided-tissue regeneration plate component of the invention to a support screw component of a snap-fit embodiment.

FIG. 4 depicts the mating of the guided-tissue regeneration plate 12 to a guided-tissue regeneration support screw 11 of the snap-fit embodiment. (The gum tissue is not shown.) The space 13 is the area where new bone will grow, the space having been created by the guided-tissue regeneration plate support and fixation system of the invention. The guided-tissue regeneration plate support screw 11 is placed into the bony ridge 3. After the guided-tissue regeneration plate 12 is affixed to the guided-tissue regeneration plate support screw 11 by snapping it in place, the plate is molded into shape by bending the edges down as shown.

Figure 5:
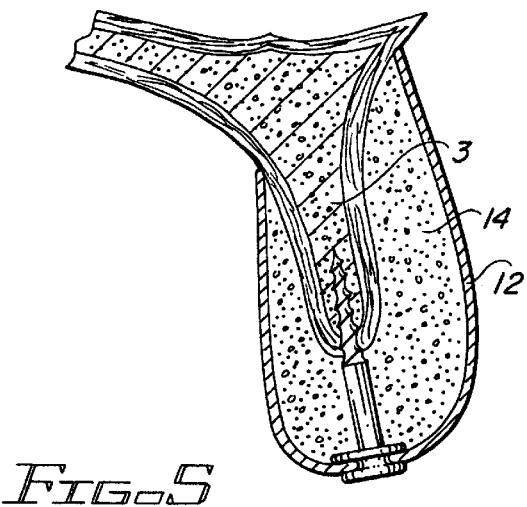
FIG. 5 shows bone graft material packed beneath the plate and against the existing bony ridge.

As shown in FIG. 5, once the guided-tissue regeneration plate 12 has been molded into place, then bone graft material 14 is packed beneath the plate 12 and against the existing bony ridge 3. After a period of approximately four-to-eight months, a new bony ridge will form within the space created by the guided-tissue regeneration plate support and fixation system. (Gum tissue not shown.)

Figure 6:
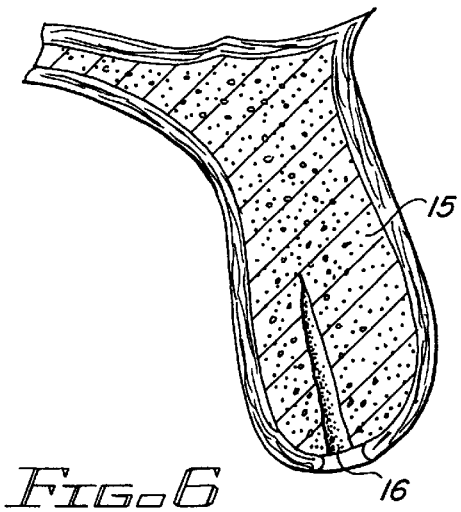
FIG. 6 shows how the bony ridge appears after the guided-tissue regeneration plate support and fixation system has been removed to expose the new bony ridge.

Thus, FIG. 6 shows how the bony ridge appears after the guided-tissue regeneration plate support and fixation system has been removed to expose the new bony ridge 15. A small hole 16 remains after the removal of the guided-tissue regeneration plate support screw. (Gum tissue not shown.)

Figure 7:
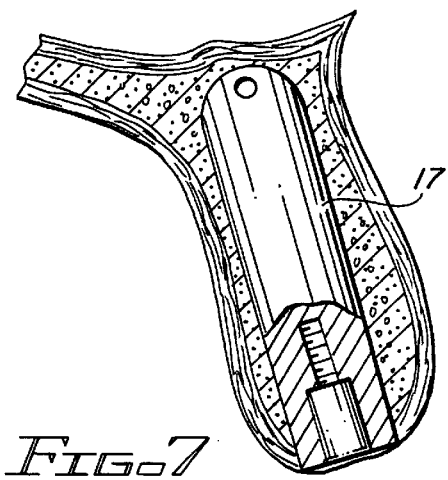
FIG. 7 depicts the placement of a large implant into the new bony ridge.

FIG. 7 depicts the placement of a large implant 17 into the new bony ridge. A tooth can be attached to the implant later.

Figure 8:
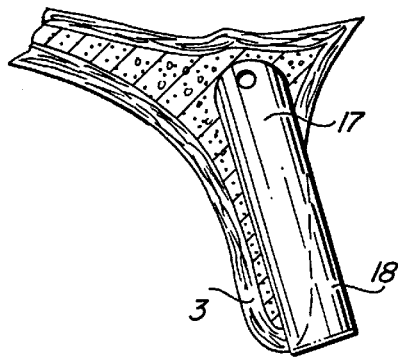
FIG. 8 shows the placement of an implant into an atrophic bony ridge.

FIG. 8 shows the placement of an implant 17 into an atrophic bony ridge 3. In this environment, the implant is not fully encased in bone resulting in an exposed area 18 of the implant outside the confines of the existing bone 3.

Figure 9:
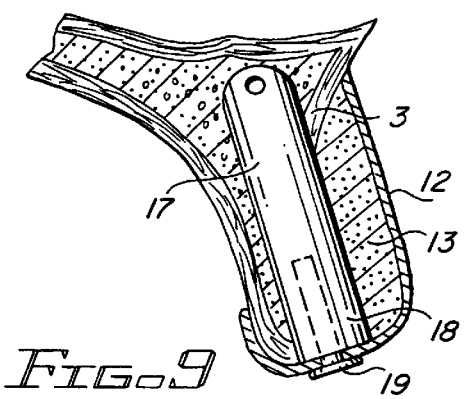
FIG. 9 depicts the installation of a guided-tissue regeneration plate using a screw supplied by an implant manufacturer.

FIG. 9 depicts the installation of a guided-tissue regeneration plate 12 by inserting the healing screw 19 supplied by the implant manufacturer which can be used in place of a tenting-type support screw to mate the guided-tissue regeneration plate 12 directly to the implant 17. This screw 19 extends through the aperture of the guided-tissue regeneration plate 12 and is thus used instead of the snap-type embodiment previously described. The space 13 created by the guided-tissue regeneration plate 12 is filled with bone graft material, thus covering the exposed portion of the dental implant 18 which is out of the confines of the existing resorbed bony ridge 3.

Figure 10:
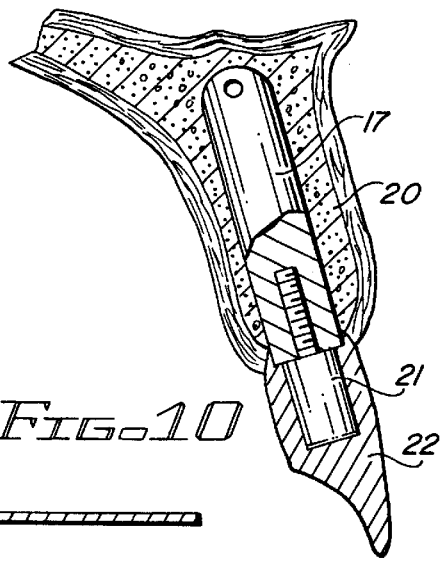
FIG. 10 illustrates the final result of the process shown progressively in FIGS. 8, 9 and 10.

FIG. 10 illustrates the final result of the process shown progressively in FIGS. 8, 9, 10 after the removal of the guided-tissue regeneration plate (not shown) by revealing that the dental implant 17 is now covered with new bone 20 that has grown around the dental implant after four-to-eight months of healing time and the subsequent removal of the guided-tissue regeneration plate system. As will be apparent to those skilled in the art, after the removal of the guided-tissue regeneration plate, a post has been placed into the dental implant 17 as normal followed by a crown or tooth 22 which is secured to the post in the well known manner.

Figure 11:
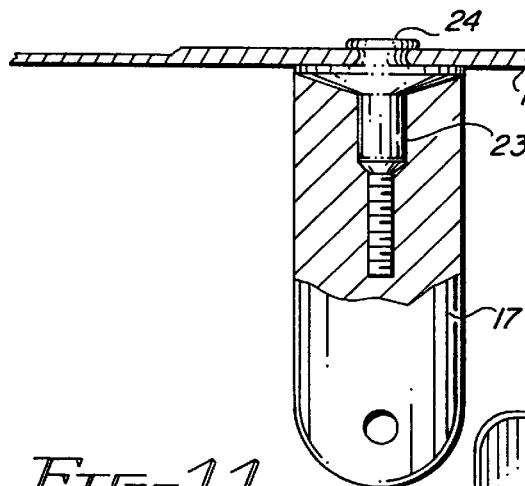
FIG. 11 illustrates the manner in which the guided-tissue regeneration plate can be snap-attached over a modified healing screw made to internally thread into a dental implant.

FIG. 11 illustrates the manner in which the guided-tissue regeneration plate 12 can be snap-attached over a modified healing screw 23 made to internally thread into a dental implant 17. The modified healing screw 23 has a receiver cap 24 adapted to receive the generally centrally disposed aperture in the guided-tissue regeneration plate 12.

Figure 12:
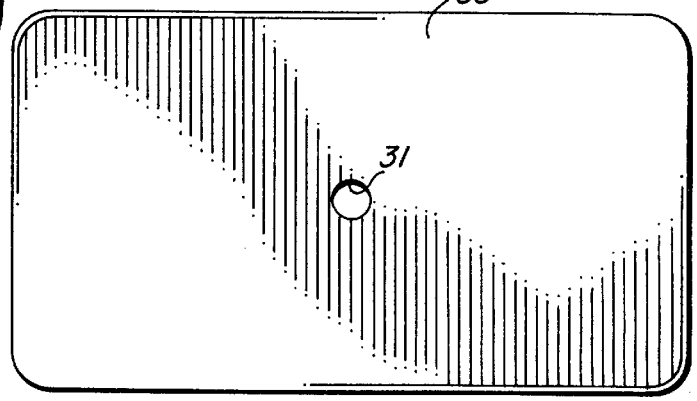
FIG. 12 depicts a non-perforated embodiment of the guided-tissue regeneration plate.

FIG. 12 depicts a non-perforated embodiment 30 of the guided-tissue regeneration plate, particularly illustrating the generally central aperture 31 by which the guided-tissue regeneration plate may be secured using a screw as previously described.

FIG. 13 depicts the snap configured support screw 11 ready to receive the guided-tissue regeneration plate 30 through the aperture 31. Attention is also directed to the cross-section of the guided-tissue regeneration plate 30 which includes a relatively thick central region 32 and a thinner peripheral region 33 as previously described.

FIG. 14 depicts the mating of the guided-tissue regeneration plate 30 over the snap configured support screw 11 after the edges have been bent down to create the space below the guided-tissue regeneration plate.

FIG. 15 illustrates a perforated version 35 of the guided-tissue regeneration plate which allows for blood supply to pass freely through the plate. Note the generally centrally disposed aperture 25.

FIG. 16 depicts a guided-tissue regeneration plate 35 being secured to a guided-tissue regeneration plate support screw 26 by a small set screw 27 which is placed through the aperture 25 in the guided-tissue regeneration plate and into the support screw 26 which has an internally threaded, axially oriented blind hole 36 in its top.

FIG. 17 illustrates the manner in which an exemplary healing screw 19 of the sort typically supplied by a dental implant manufacturer can be employed to secure the guided-tissue regeneration plate 12 to the dental implant 17.

Thus, while the principles of the invention have now been made clear in an illustrative embodiment, there will be immediately obvious to those skilled in the art many modifications of structure, arrangements, proportions, the elements, materials, and components, used in the practice of the invention which are particularly adapted for specific environments and operating requirements without departing from those principles.

What is claimed is:

1. A method of growing bone in order to increase the volume of the bony ridge of the maxilla or mandible by creating a protected and supported space between the underside of the gum tissue and the jaw bone which is protected from outside chewing forces, muscular or tissue pressure, or any other premature loading by utilizing a guided-tissue regeneration plate support and fixation system, which method comprises:

A) fixing a bone screw to the jaw bone, the bone screw including a head configured as a receiver cap to receive and intimately mate with a guided-tissue regeneration plate, the bone screw being further characterized in that:
  1) it is fabricated from a bio-compatible material selected from the group including titanium, chromium cobalt alloy and polytetrafluoraethylene-coated surgical steel; and
  2) is configured with an undercut area on the head of the bone screw in order to snappingly receive the centrally located aperture and thus securely retain the guided-tissue regeneration plate;
B) securing a perforated guided-tissue regeneration plate to the jaw bone, which guided-tissue regeneration plate is pliable, easily bendable and moldable, but keeps its shape after being molded, the guided-tissue regeneration plate being further characterized in that it is fabricated from a bio-compatible material selected from the group including titanium, chromium cobalt alloy and polytetrafluoraethylene-coated surgical steel and has a periphery and a generally centrally located aperture for the purpose of intimate attachment and direct fixation to the bone screw head, thereby creating an indirect fixation of the guided-tissue regeneration plate to the jaw bone and a direct fixation of the bone screw to the jaw bone, the perforations being characterized in that they are of sufficient size as to promote the exchange of nutrients and blood supply across the guided-tissue regeneration plate;
C) coupling the guided-tissue regeneration plate to the bone screw to thereby establish a protected space for bone growth such that the bone screw head functions as a receiver cap configured to receive and to be intimately mated with the guided-tissue regeneration plate while at the same time supporting and securing the guided-tissue regeneration plate in a tenting fashion a predetermined distance from the bony ridge; and
D) waiting for bone to grow in the resulting protected space.

2. The method of claim 1 in which the guided-tissue regeneration plate and the bone screw are made of Grade 1 titanium.

3. The method of claim 1 in which the guided-tissue regeneration plate is coated with a resorbable, bio-compatible material for the purpose of creating a temporary guided-tissue regeneration plate barrier to prevent migration of epithelial cells through the perforations, yet allow blood supply and/or nutrients to pass through the resorbable barrier.

4. The method of claim 1 in which the thickness of the guided-tissue regeneration plate in the region of the periphery thereof is within the range of five to ten thousandths of an inch and the guided-tissue regeneration plate is stiffer and more rigid in the region proximate the generally centrally located aperture such that the guided-tissue regeneration plate is stiffer in the region proximate the generally centrally located aperture and more pliable toward the periphery to facilitate adequate support adjacent the generally centrally located aperture, which support is thereby coupled to the bone screw and underlying bony ridge while achieving adequate flexibility and moldability in the region of the periphery of the guided-tissue regeneration plate.

5. The method of claim 1 in which the generally centrally located aperture is at least fifty thousandths of an inch in diameter.

6. The method of claim 1 in which the bone screw is sharply pointed with a cutting flute at its tip to allow for self-threading.

7. The method of claim 1 in which the bone screw has a major/minor diameter ratio of its threads that is at least two in order to facilitate secure anchorage to the bone.

8. A method of growing bone in order to increase the volume of the bony ridge of the maxilla or mandible by creating a protected and supported space between the underside of the gum tissue and the jaw bone which is protected from outside chewing forces, muscular or tissue pressure, or any other premature loading by utilizing a guided-tissue regeneration plate support and fixation system, which method comprises:
  A) fixing a bone screw to the jaw bone, the bone screw including a head configured as a receiver cap to receive and intimately mate with a guided-tissue regeneration plate, the bone screw being further characterized in that:
    1) it is fabricated from a bio-compatible material selected from the group including titanium, chromium cobalt alloy and polytetrafluoraethylene-coated surgical steel; and
    2) has a portion of the shaft near the head that is not threaded in order to create a stop and seat as the bone screw threads into the bone to facilitate better anchorage of the bone screw and fixing the distance from the bony ridge to the guided-tissue regeneration plate in the region of the bone screw;
  B) securing a perforated guided-tissue regeneration plate to the jaw bone, which guided-tissue regeneration plate is pliable, easily bendable and moldable, but keeps its shape after being molded, the guided-tissue regeneration plate being further characterized in that it is fabricated from a bio-compatible material selected from the group including titanium, chromium cobalt alloy and polytetrafluoraethylene-coated surgical steel and has a periphery and a generally centrally located aperture for the purpose of intimate attachment and direct fixation to the bone screw head, thereby creating an indirect fixation of the guided-tissue regeneration plate to the jaw bone and a direct fixation of the bone screw to the jaw bone, the perforations being characterized in that they are of sufficient size as to promote the exchange of nutrients and blood supply across the guided-tissue regeneration plate;
  C) coupling the guided-tissue regeneration plate to the bone screw to thereby establish a protected space for bone growth such that the bone screw head functions as a receiver cap configured to receive and to be intimately mated with the guided-tissue regeneration plate while at the same time supporting and securing the guided-tissue regeneration plate in a tenting fashion a predetermined distance from the bony ridge; and
  D) waiting for bone to grow in the resulting protected space.

9. The method of 8 in which the bone screw is fabricated with an internally threaded aperture on its head to receive an additional micro fastening screw in order to receive the guided-tissue regeneration plate and the micro fastening screw.

10. Apparatus for use in conjunction with the practice of a method of growing bone in order to increase the volume of the bony ridge of the maxilla or mandible by creating a protected and supported space between the underside of the gum tissue and the jaw bone which is protected from outside chewing forces, muscular or tissue pressure, or any other premature loading, which apparatus comprises:
  A) a bone screw provided with a head configured as a receiver cap to receive and intimately mate with a guided-tissue regeneration plate, said bone screw being further characterized in that:
1) it is fabricated from a bio-compatible material selected from the group including titanium, chromium cobalt alloy and polytetrafluoraethylene-coated surgical steel; and
2) is configured with a snap undercut area on head of said bone screw in order to snappingly receive said centrally located aperture and thus securely retain said guided-tissue regeneration plate; and
B) said guided-tissue regeneration plate being perforated and fabricated from a pliable, easily bendable material which retains its shape after molding, said guided-tissue regeneration plate having a periphery and a generally centrally located aperture dimensioned and configured to intimately receive said bone screw head such that said guided-tissue regeneration plate is directly supported by said bone screw and indirectly supported by the jaw bone; said guided-tissue regeneration plate being further characterized in that it is fabricated from a bio-compatible material selected from the group including titanium, chromium cobalt alloy and polytetrafluoraethylene-coated surgical steel, said perforations being characterized in that they are of sufficient size as to promote the exchange of nutrients and blood supply across the guided-tissue regeneration plate;
such that said bone screw head functions as a receiver cap configured to receive and to be intimately mated with said guided-tissue regeneration plate while at the same time supporting and securing said guided-tissue regeneration plate in a tenting fashion a predetermined distance from the bony ridge while bone grows in the resulting protected space.

11. The apparatus of claim 10 in which said guided-tissue regeneration plate and said support medium are made of titanium.

12. The apparatus of claim 10 in which said guided-tissue regeneration plate is coated with a resorbable, bio-compatible material for the purpose of creating a temporary guided-tissue regeneration plate barrier to prevent migration of epithelial cells through the perforations, yet allow blood supply and/or nutrients to pass through the said resorbable barrier.

13. The apparatus of claim 10 in which the thickness of said guided-tissue regeneration plate in the region of the periphery thereof is within the range of five to ten thousandths of an inch and the guided-tissue regeneration plate is stiffer and more rigid in the region proximate said generally centrally located aperture such that the guided-tissue regeneration plate is stiffer in the region proximate the generally centrally located aperture and more pliable toward said periphery to facilitate adequate support adjacent said generally centrally located aperture, which support is thereby coupled to said bone screw and underlying bony ridge while achieving adequate flexibility and moldability in the region of said periphery of said guided-tissue plate.

14. The apparatus of claim 10 in which said generally centrally located aperture is at least fifty thousandths of an inch in diameter.

15. The apparatus of claim 10 in which said bone screw is sharply pointed with a cutting flute at its tip to allow for self-threading.

16. The apparatus of claim 10 in which said bone screw has a major/minor diameter ratio of its threads that is at least two in order to facilitate secure anchorage to the bone.

17. Apparatus for use in conjunction with the practice of a method of growing bone in order to increase the volume of the bony ridge of the maxilla or mandible by creating a protected and supported space between the underside of the gum tissue and the jaw bone which is protected from outside chewing forces, muscular or tissue pressure, or any other premature loading, which apparatus comprises:
A) a bone screw provided with a head configured as a receiver cap to receive and intimately mate with a guided-tissue regeneration plate, said bone screw being further characterized in that:
1) it is fabricated from a bio-compatible material selected from the group including titanium, chromium cobalt alloy and polytetrafluoraethylene-coated surgical steel; and
2) has a portion of the shaft near said head that is not threaded in order to create a stop and seat as said bone screw threads into the bone to facilitate better anchorage of said bone screw and establishing the distance from the bony ridge to said guided-tissue regeneration plate in the region of said bone screw
B) said guided-tissue regeneration plate being perforated and fabricated from a pliable, easily bendable material which retains its shape after molding, said guided-tissue regeneration plate having a periphery and a generally centrally located aperture dimensioned and configured to intimately receive said bone screw head such that said guided-tissue regeneration plate is directly supported by said bone screw and indirectly supported by the jaw bone; said guided-tissue regeneration plate being further characterized in that it is fabricated from a bio-compatible material selected from the group including titanium, chromium cobalt alloy and polytetrafluoraethylene-coated surgical steel, said perforations being characterized in that they are of sufficient size as to promote the exchange of nutrients and blood supply across the guided-tissue regeneration plate;
such that said bone screw head functions as a receiver cap configured to receive and to be intimately mated with said guided-tissue regeneration plate while at the same time supporting and securing said guided-tissue regeneration plate in a tenting fashion a predetermined distance from the bony ridge while bone grows in the resulting protected space.

18. The apparatus of claim 10 in which said bone screw is fabricated with an internally threaded aperture on its head to receive an additional micro fastening screw in order to receive said guided-tissue regeneration plate and said micro fastening screw.

19. A method of growing bone in order to increase the volume of the bony ridge of the maxilla or mandible by creating a protected and supported space between the underside of the gum tissue and the jaw bone which is protected from outside chewing forces, muscular or tissue pressure, or any other premature loading by utilizing a guided-tissue regeneration plate support and fixation system, which method comprises:
A) fixing a bone screw to the jaw bone, the bone screw including a head configured as a receiver cap to receive and intimately mate with a guided-tissue regeneration plate, the bone screw being further characterized in that it:
1) is fabricated from titanium;
2) is sharply pointed with a cutting flute at its tip to allow for self-threading; and
3) has a major/minor diameter ratio of its threads that is at least two in order to facilitate secure anchorage to the jaw bone; and B) securing a perforated guided-tissue regeneration plate to the bone screw, which guided-tissue regeneration plate is pliable, easily bendable and moldable, but keeps its shape and is rigid after molded, the guided-tissue regeneration plate being further characterized in that it:
1) is fabricated from titanium;
2) has a generally centrally located aperture at least fifty thousandths of an inch in diameter for the purpose of intimate attachment and direct fixation to the bone screw head, thereby creating an indirect fixation of the guided-tissue regeneration plate to the jaw bone and a direct fixation of the bone screw to the jaw bone;
3) is relatively rigid in the region proximate the generally centrally located aperture and is relatively pliable in the region toward its periphery to facilitate adequate support adjacent the generally centrally located aperture, which support is thereby coupled to the underlying support medium while achieving adequate flexibility and moldability in the region of the periphery of the guided-tissue regeneration plate; and
4) includes perforations of sufficient size as to promote the exchange of nutrients and blood supply across the guided-tissue regeneration plate;

C) configuring the bone screw with a snap undercut area on the head of the screw in order to snappingly receive the centrally located aperture and securely retain the guided-tissue regeneration plate;

D) coupling the guided-tissue regeneration plate to the bone screw to thereby establish a protected space for bone growth such that the bone screw head functions as a receiver cap configured to receive and to be intimately mated with the guided-tissue regeneration plate while at the same time supporting and securing the guided-tissue regeneration plate in a tenting fashion a predetermined distance from the bony ridge; and E) waiting for bone to grow in the protected space.

20. The method of claim 19 in which respective relatively rigid and relatively pliable regions of the guided tissue regeneration plate are achieved by fabricating the guided tissue regeneration plate to be thicker in the region proximate the generally centrally located aperture than in the region toward its periphery.

21. The method of claim 19 in which respective relatively rigid and relatively pliable regions of the guided tissue regeneration plate are achieved by fabricating the guided tissue regeneration plate to have a lower concentration of the perforations in the region proximate the generally centrally located aperture than in the region toward its periphery.

22. Apparatus for use in conjunction with the practice of a method of growing bone in order to increase the volume of the bony ridge of the maxilla or mandible by creating a protected and supported space between the underside of the gum tissue and the jaw bone which is protected from outside chewing forces, muscular or tissue pressure, or any other premature loading, which apparatus comprises:

A) a bone screw, said bone screw including a head configured as a receiver cap to receive and intimately mate with a guided-tissue regeneration plate, said bone screw being further characterized in that it:
1) is fabricated from titanium;
2) is sharply pointed with a cutting flute at its tip to allow for self-threading; and
3) has a major/minor diameter ratio of its threads that is at least two in order to facilitate secure anchorage to the bone; and B) a guided-tissue regeneration plate, said guided-tissue regeneration plate:
1) being fabricated from titanium;
2) having a periphery and a generally centrally located aperture at least fifty thousandths of an inch in diameter for the purpose of intimate attachment and direct fixation to said bone screw head, thereby creating an indirect fixation of said guided-tissue regeneration plate to the jaw bone and a direct fixation of said bone screw to the jaw bone;
3) being relatively rigid in the region proximate said generally centrally located aperture and relatively pliable toward said periphery to facilitate adequate support adjacent said generally centrally located aperture, which support is thereby coupled to the underlying jaw bone while achieving adequate flexibility and moldability in the region of said periphery of said guided-tissue regeneration plate; and
4) being perforated with perforations characterized in that they are of sufficient size as to promote the exchange of nutrients and blood supply across the guided-tissue regeneration plate; and C) said bone screw being configured with a snap undercut area on the head of the screw in order to snappingly receive the centrally located aperture and securely retain the guided-tissue regeneration plate;

such that said bone screw head functions as a receiver cap configured to receive and to be intimately mated with said guided-tissue regeneration plate while at the same time supporting and securing said guided-tissue regeneration plate in a tenting fashion a predetermined distance from the bony ridge while bone grows in the resulting protected space.

23. The apparatus of claim 22 in which said respective relatively rigid and relatively pliable regions of said guided tissue regeneration plate are achieved by fabricating said guided tissue regeneration plate to be thicker in the region proximate said generally centrally located aperture than in the region toward its said periphery.

24. The apparatus of claim 22 in which said respective relatively rigid and relatively pliable regions of said guided tissue regeneration plate are achieved by fabricating said guided tissue regeneration plate to have a lower concentration of said perforations in said region proximate said generally centrally located aperture than in said region toward its periphery.

* * * * *